(12) United States Patent
Liu et al.

(10) Patent No.: US 10,617,893 B2
(45) Date of Patent: *Apr. 14, 2020

(54) BEAM SHAPING ASSEMBLY FOR NEUTRON CAPTURE THERAPY

(71) Applicant: NEUBORON MEDTECH LTD., Nanjing, Jiangsu (CN)

(72) Inventors: Yuan-hao Liu, Jiangsu (CN); Wei-lin Chen, Jiangsu (CN); Pei-yi Lee, Jiangsu (CN); Ming-chuan Chang, Jiangsu (CN); Wenyu Xu, Jiangsu (CN)

(73) Assignee: NEUBORON MEDTECH LTD., Nanjing, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/401,328

(22) Filed: May 2, 2019

(65) Prior Publication Data
US 2020/0023205 A1 Jan. 23, 2020

Related U.S. Application Data

(63) Continuation of application No. 15/704,495, filed on Sep. 14, 2017, now Pat. No. 10,328,286, which is a
(Continued)

(30) Foreign Application Priority Data

May 4, 2015 (CN) .......................... 2015 1 0222234
May 4, 2015 (CN) ...................... 2015 2 0281118 U
(Continued)

(51) Int. Cl.
A61N 5/10 (2006.01)
G21G 4/02 (2006.01)
(Continued)

(52) U.S. Cl.
CPC .......... *A61N 5/1077* (2013.01); *A61N 5/1042* (2013.01); *C04B 35/553* (2013.01);
(Continued)

(58) Field of Classification Search
CPC ................ H05H 3/06; A61N 2005/109; A61K 41/0095; G01N 2223/106
(Continued)

(56) References Cited

U.S. PATENT DOCUMENTS 5,703,918 A 12/1997 Hiismake et al.
10,328,286 B2 * 6/2019 Liu .......................... G21K 5/04
2016/0220839 A1 8/2016 Kuri et al.

FOREIGN PATENT DOCUMENTS

CN 104372191 A 2/2015
CN 104511096 A 4/2015
(Continued)

OTHER PUBLICATIONS

International Search Report for PCT/CN2016/079568, dated Jul. 21, 2016.
(Continued)

*Primary Examiner* — David A Vanore
(74) *Attorney, Agent, or Firm* — Locke Lord LLP; Tim Tingkang Xia, Esq.

(57) ABSTRACT

A beam shaping assembly for neutron capture therapy includes a beam inlet, a target having nuclear reaction with an incident proton beam from the beam inlet to produce neutrons forming a neutron beam, a moderator adjoining to the target, a reflector surrounding the moderator, a thermal neutron absorber adjoining to the moderator, a radiation shield arranged inside the beam shaping assembly and a beam outlet. The material of the moderator is subjected to a powder sintering process using a powder sintering device so as to change powders or a power compact into blocks. The
(Continued)

reflector leads the neutrons deviated from the main axis back. The thermal neutron absorber is used for absorbing thermal neutrons so as to avoid overdosing in superficial normal tissue during therapy. The radiation shield is used for shielding leaking neutrons and photons so as to reduce dose of the normal tissue not exposed to irradiation.

20 Claims, 5 Drawing Sheets

Related U.S. Application Data continuation of application No. PCT/CN2016/079568, filed on Apr. 18, 2016.

(30) Foreign Application Priority Data

Sep. 11, 2015 (CN) .......................... 2015 1 0579928
Sep. 11, 2015 (CN) ...................... 2015 2 0706407 U

(51) Int. Cl.
C04B 35/553 (2006.01)
C04B 35/645 (2006.01)
G21K 5/04 (2006.01)

(52) U.S. Cl.
CPC ........ *C04B 35/645* (2013.01); *C04B 35/6455* (2013.01); *G21G 4/02* (2013.01); *G21K 5/04* (2013.01); *A61N 2005/109* (2013.01); *A61N 2005/1094* (2013.01); *A61N 2005/1095* (2013.01)

(58) Field of Classification Search
USPC ..... 250/492.1, 492.3, 505.1, 518.1; 600/427, 600/436, 476
See application file for complete search history.

(56) References Cited

FOREIGN PATENT DOCUMENTS

| | | |
|---|---|---|
| CN | 104548388 A | 4/2015 |
| CN | 104640824 A | 5/2015 |
| CN | 204319539 U | 5/2015 |
| CN | 204798657 U | 11/2015 |
| EP | 1895819 A1 | 3/2008 |
| EP | 2805745 A1 | 11/2014 |
| EP | 2865658 A1 | 4/2015 |
| JP | H10251070 A | 9/1998 |
| JP | 2012236379 A | 12/2012 |
| WO | 9429881 A1 | 12/1994 |
| WO | 2015005006 A1 | 1/2015 |

OTHER PUBLICATIONS

M.H. Moghim et al., Hot-pressing of bimodally distributed magnesium fluoride powder, Infrared Physics & Technology, 2010, 53, 430-433.
European Patent Office, "Search Report", dated Oct. 30, 2018, Germany.
European Patent Office, "Search Report", dated Mar. 15, 2018, Germany.
Table of Isotopic Masses and Natural Abundances.

* cited by examiner

BEAM SHAPING ASSEMBLY FOR NEUTRON CAPTURE THERAPY

RELATED APPLICATION INFORMATION

This application is a continuation application of U.S. patent application Ser. No. 15/704,495, filed in the U.S. on Sep. 14, 2017 ("Parent Application"), which is a continuation of International Application No. PCT/CN2016/079568, filed on Apr. 18, 2016, which claims priority to Chinese Patent Application No. 201510222234.5, filed on May 4, 2015; Chinese Patent Application No. 201520281118.6, filed on May 4, 2015; Chinese Patent Application No. 201510579928.4, filed on Sep. 11, 2015; and Chinese Patent Application No. 201520706407.6, filed on Sep. 11, 2015, the disclosures of which are hereby incorporated by reference.

FIELD OF THE DISCLOSURE

The present disclosure relates generally to a beam shaping assembly, and, more particularly, to a beam shaping assembly for neutron capture therapy.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

BNCT takes advantage that the boron ($^{10}$B)-containing pharmaceuticals have high neutron capture cross section and produces $^4$He and $^7$Li heavy charged particles through $^{10}$B(n,$\alpha$)$^7$Li neutron capture and nuclear fission reaction. As illustrated in FIGS. 1 and 2, a schematic drawing of BNCT and a nuclear reaction formula of $^{10}$B (n,$\alpha$) $^7$Li neutron capture are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

BNCT is also well known for binary cancer therapy, for its effectiveness depending on the concentration of the boronated pharmaceuticals and the number of the thermal neutrons at the tumor site. Thus, besides development of the boronated pharmaceuticals, improvement of flux and quality of the neutron source plays a significant role in BNCT researches.

The statements in this section merely provide background information related to the present disclosure and may not constitute prior art.

SUMMARY

In order to improve flux and quality of the neutron source, an aspect of the present disclosure provides a beam shaping assembly for neutron capture therapy includes: a beam inlet; a target, wherein the target has nuclear reaction with an incident proton beam from the beam inlet to produce neutrons, and wherein the neutrons form a neutron beam defining a main axis; a moderator adjoining to the target, wherein the neutrons are moderated by the moderator to epithermal neutron energies, the material of the moderator is prepared by mixing a mixture containing one or more of $PbF_4$, $Al_2O_3$, $AlF_3$, $CaF_2$ and $MgF_2$ and a $^6$Li element-containing material accounting for 0.1 to 5% in percentage by weight of the mixture, and wherein the material of the moderator is subjected to a powder sintering process using a powder sintering device so as to change powders or powder compacts into blocks; a reflector surrounding the moderator, wherein the reflector leads the neutrons deviated from the main axis back to enhance epithermal neutron beam intensity; a thermal neutron absorber adjoining to the moderator, wherein the thermal neutron absorber is used for absorbing thermal neutrons so as to avoid overdosing in superficial normal tissue during therapy; a radiation shield arranged inside the beam shaping assembly, and wherein the radiation shield is used for shielding leaking neutrons and photons so as to reduce dose of the normal tissue not exposed to irradiation; and a beam outlet.

Implementations of this aspect may include one or more of the following features.

The incident proton beam is accelerated by means of an accelerator to overcome coulomb repulsion energy of a target atomic nucleus and generate nuclear reaction with the target to produce neutrons, and the target is made of a metal material.

An epithermal neutron energy range ranges from 0.5 eV to 40 keV, a thermal neutron energy range is below 0.5 eV, and a fast neutron energy range is above 40 keV, and the beam shaping assembly reduces the quantity of thermal neutrons and fast neutrons; and wherein the reflector is made of a material having a high neutron reflection ability, and the thermal neutron absorber is made of a material having a cross section for acting with thermal neutrons.

More particularly, the reflector is made of at least one of Pb or Ni.

More particularly, the thermal neutron absorber is made of $^6$Li, and an air passage is arranged between the thermal neutron absorber and the beam outlet.

More particularly, the radiation shield may include a photon shield and a neutron shield.

Further, an outer surface of the moderator may include a first tapered section and a second tapered section adjoining to the first tapered section, and a tapering direction of the first tapered section is opposite to a tapering direction of the second tapered section, and wherein the first tapered section may include a first side and a second side facing away from the beam outlet and is tapered gradually from the second side towards the first side, and the second tapered section may include a third side and a fourth side facing the beam outlet and is tapered gradually from the third side towards the fourth side.

More particularly, the first side defines a first diameter perpendicularly to the main axis, the second side and the third side defines a second diameter perpendicularly to the main axis and the fourth side defines a third diameter perpendicularly to the main axis, the first diameter is 1 cm to 20 cm in length, the second diameter is 30 cm to 100 cm in length, the third diameter is 1 cm to 50 cm in length, and wherein multiple sintered blocks are connected to form the moderator and a density of the moderator is 80 to 100 percent of theoretical density.

Further, the powder sintering device is a hot-press sintering device or a spark plasma sintering device, and the powder sintering process is a hot-press sintering process or a spark plasma sintering process.

More particularly, the hot-press sintering device may include a heating furnace, a pressing assembly arranged in the heating furnace, a mold, powders or powder compacts loaded in the mold, and a controller for controlling the normal operation of the hot-press sintering device, and the hot-press sintering process may include the following steps: filling the mold with a predetermined amount of powders or powder compacts; starting the hot-press furnace to preset pressure and temperature parameters; moving the pressing assembly to press the powders or powder compacts in the mold; controlling the hot-press sintering device by the controller to be under the condition of normal operation; and switching on power to sinter the powders or powder compacts into blocks.

More particularly, the spark plasma sintering device may include a first electrode, a second electrode, a conductive mold arranged between the first electrode and the second electrode, a pulse current generator for providing pulse current for the mold, a pressing assembly with a pressing member for pressing, and a controller for controlling the pulse current generator and the pressing assembly, wherein at least one of the first electrode and the second electrode is moved with respect to the other one, and at least one of the first electrode and the second electrode is connected to the pressing assembly, so that the powders or powder compacts in the mold are pressed; and the spark plasma sintering process comprises the following steps: filling the mold with a predetermined amount of powders or powder compacts; moving at least one of the first electrode and the second electrode to press the powders or the powder compacts in the mold; switching on the pulse current generator to conduct electricity to the conductive mold, so that plasma is generated, and thereby the surfaces of the powders or the powder compacts are activated and heat; and sintering the powders or the powder compacts into blocks.

Further, the spark plasma sintering device further includes a position measurement system for measuring the position of the pressing member, an atmosphere control system for controlling atmosphere in the mold, a water cooling system for cooling the spark plasma sintering device, and a temperature measurement system for measuring temperature in the spark plasma sintering device, and the spark plasma sintering process further includes the following steps: controlling the position measurement system by the controller in order to ensure the normal operation of the position measurement system, controlling the atmosphere control system by the controller in order to ensure that atmosphere in the mold is under the condition of normal operation, controlling the water cooling system by the controller in order to ensure the normal operation of the water cooling system, and controlling the temperature measurement system by the controller in order to ensure that temperature in the spark plasma sintering device is under the condition of normal operation.

In another aspect of the present disclosure, a beam shaping assembly for neutron capture therapy is provided for improving flux and quality of the neutron source. The beam shaping assembly includes a beam inlet; a target, wherein the target has nuclear reaction with an incident proton beam from the beam inlet to produce neutrons, and wherein the neutrons form a neutron beam defining a main axis; a moderator adjoining to the target, wherein the neutrons are moderated by the moderator to epithermal neutron energies, the material of the moderator is prepared from a material containing at least one of $LiF$, $Li_2CO_3$, $Al_2O_3$, $AlF_3$, $CaF_2$ and $MgF_2$, wherein the material of the moderator is subjected to a powder sintering process using a powder sintering device so as to change powders or powder compacts into blocks; a reflector surrounding the moderator, wherein the reflector leads the neutrons deviated from the main axis back to enhance epithermal neutron beam intensity; a thermal neutron absorber adjoining to the moderator, wherein the thermal neutron absorber is used for absorbing thermal neutrons so as to avoid overdosing in superficial normal tissue during therapy; a radiation shield arranged inside the beam shaping assembly, wherein the radiation shield is used for shielding leaking neutrons and photons so as to reduce dose of the normal tissue not exposed to irradiation; and a beam outlet.

Further, the outer surface of the moderator may include the first tapered section and a second tapered section adjoining to the first tapered section, and a tapering direction of the first tapered section is opposite to a tapering direction of the second tapered section, and wherein the first tapered section may include a first side and a second side facing away from the beam outlet and is tapered gradually from the second side towards the first side, and the second tapered section may include a third side and a fourth side facing the beam outlet and is tapered gradually from the third side towards the fourth side.

More particularly, the first side defines a first diameter perpendicularly to the main axis, the second side and the third side defines a second diameter perpendicularly to the main axis and the fourth side defines a third diameter perpendicularly to the main axis, the first diameter is 1 cm to 20 cm in length, the second diameter is 30 cm to 100 cm in length, the third diameter is 1 cm to 50 cm in length, and wherein multiple sintered blocks are connected to form the moderator and a density of the moderator is 80 to 100 percent of theoretical density.

Further, the powder sintering device is a hot-press sintering device or a spark plasma sintering device, and the powder sintering process is a hot-press sintering process or a spark plasma sintering process. Wherein the hot-press sintering device includes a heating furnace, a pressing assembly arranged in the heating furnace, a mold, powders or powder compacts loaded in the mold, and a controller for controlling the normal operation of the hot-press sintering device, and the hot-press sintering process includes the following steps: filling the mold with a predetermined amount of powders or powder compacts; starting the hot-press furnace to preset pressure and temperature parameters;

moving the pressing assembly to press the powders or powder compacts in the mold; controlling the hot-press sintering device by the controller to be under the condition of normal operation; and switching on power to sinter the powders or powder compacts into blocks. And wherein the spark plasma sintering device includes a first electrode, a second electrode, a conductive mold arranged between the first electrode and the second electrode, a pulse current generator for providing pulse current for the mold, a pressing assembly with a pressing member for pressing, and a controller for controlling the pulse current generator and the pressing assembly, wherein at least one of the first electrode and the second electrode is moved with respect to the other one and connected to the pressing assembly, so that the powders or powder compacts in the mold are pressed; and the spark plasma sintering process includes the following steps: filling the mold with a predetermined amount of powders or powder compacts; moving at least one of the first electrode and the second electrode to press the powders or the powder compacts in the mold; switching on the pulse current generator to conduct electricity to the conductive mold, so that plasma is generated, and thereby the surfaces of the powders or the powder compacts are activated and heat; and sintering the powders or the powder compacts into blocks.

More particularly, the spark plasma sintering device further includes a position measurement system for measuring the position of the pressing member, an atmosphere control system for controlling atmosphere in the mold, a water cooling system for cooling the spark plasma sintering device, and a temperature measurement system for measuring temperature in the spark plasma sintering device, and the spark plasma sintering process further includes the following steps: controlling the position measurement system by the controller in order to ensure the normal operation of the position measurement system, controlling the atmosphere control system by the controller in order to ensure that atmosphere in the mold is under the condition of normal operation, controlling the water cooling system by the controller in order to ensure the normal operation of the water cooling system, and controlling the temperature measurement system by the controller in order to ensure that temperature in the spark plasma sintering device is under the condition of normal operation.

In yet another aspect of the present disclosure, a beam shaping assembly for neutron capture therapy is provided for improving flux and quality of the neutron source. The beam shaping assembly for neutron capture therapy includes a beam inlet; a target, wherein the target has nuclear reaction with an incident proton beam from the beam inlet to produce neutrons, and wherein the neutrons form a neutron beam defining a main axis; a moderator adjoining to the target, wherein the neutrons are moderated by the moderator to epithermal neutron energies, the material of the moderator is prepared from a material containing at least one of LiF, $Li_2CO_3$, $Al_2O_3$, $AlF_3$, $CaF_2$ and $MgF_2$, wherein the material of the moderator is subjected to a powder sintering process using a powder sintering device so as to change powders or powder compacts into blocks, and wherein the powder sintering device is a hot-press sintering device or a spark plasma sintering device, and the powder sintering process is a hot-press sintering process or a spark plasma sintering process; a reflector surrounding the moderator, wherein the reflector leads the neutrons deviated from the main axis back to enhance epithermal neutron beam intensity; a thermal neutron absorber adjoining to the moderator, wherein the thermal neutron absorber is used for absorbing thermal neutrons so as to avoid overdosing in superficial normal tissue during therapy; a radiation shield arranged inside the beam shaping assembly, wherein the radiation shield is used for shielding leaking neutrons and photons so as to reduce dose of the normal tissue not exposed to irradiation; and a beam outlet.

Further, the outer surface of the moderator may include the first tapered section and a second tapered section adjoining to the first tapered section, and a tapering direction of the first tapered section is opposite to a tapering direction of the second tapered section, and wherein the first tapered section may include a first side and a second side facing away from the beam outlet and is tapered gradually from the second side towards the first side, and the second tapered section may include a third side and a fourth side facing the beam outlet and is tapered gradually from the third side towards the fourth side, and wherein the first side defines a first diameter perpendicularly to the main axis, the second side and the third side defines a second diameter perpendicularly to the main axis and the fourth side defines a third diameter perpendicularly to the main axis, the first diameter is 1 cm to 20 cm in length, the second diameter is 30 cm to 100 cm in length, the third diameter is 1 cm to 50 cm in length, and wherein multiple sintered blocks are connected to form the moderator and a density of the moderator is 80 to 100 percent of theoretical density.

More particularly, the hot-press sintering device may include a heating furnace, a pressing assembly arranged in the heating furnace, a mold, powders or powder compacts loaded in the mold, and a controller for controlling the normal operation of the hot-press sintering device, and the hot-press sintering process may include the following steps: filling the mold with a predetermined amount of powders or powder compacts; starting the hot-press furnace to preset pressure and temperature parameters; moving the pressing assembly to press the powders or powder compacts in the mold; controlling the hot-press sintering device by the controller to be under the condition of normal operation; and switching on power to sinter the powders or powder compacts into blocks; and wherein the spark plasma sintering device may include a first electrode, a second electrode, a conductive mold arranged between the first electrode and the second electrode, a pulse current generator for providing pulse current for the mold, a pressing assembly with a pressing member for pressing, and a controller for controlling the pulse current generator and the pressing assembly, wherein at least one of the first electrode and the second electrode is moved with respect to the other one and connected to the pressing assembly, so that the powders or powder compacts in the mold are pressed; and the spark plasma sintering process may include the following steps: filling the mold with a predetermined amount of powders or powder compacts; moving at least one of the first electrode and the second electrode to press the powders or the powder compacts in the mold; switching on the pulse current generator to conduct electricity to the conductive mold, so that plasma is generated, and thereby the surfaces of the powders or the powder compacts are activated and heat; and sintering the powders or the powder compacts into blocks.

The term 'cylindrical' or 'cylindrical section' referred in the embodiment of the present disclosure is an element with the contour in a substantially unchanged trend from one side to the other side along the illustrated direction. One of contour lines may be a line segment, like a corresponding one of the cylinder, or may be a high-curvature arc approximate to the line segment, like a corresponding one of a sphere with high curvature. The integral surface of the contour may be continuously connected or not if the surface of the cylinder or the high-curvature sphere is provided with many protrusions and grooves.

The term 'tapered' or 'tapered section' referred in the embodiment of the present disclosure is an element with the contour in a tapering trend from one to the other side along the illustrated direction. One of contour lines may be a line segment, like a corresponding one of the cone, or may be an arc, like a corresponding one of the sphere, and the integral surface of the contour may be continuously connected or not if the surface of the cone shape or the spherical shape is provided with plenty of protrusions and grooves.

Further areas of applicability will become apparent from the description provided herein. It should be understood that the description and specific examples are intended for purposes of illustration only and are not intended to limit the scope of the present disclosure.

Figure 1:
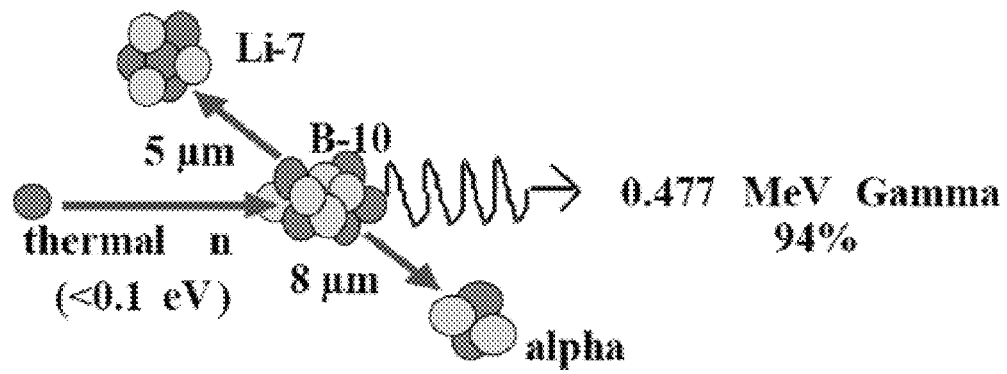
FIG. 1 is a schematic view of boron neutron capture reaction.
Figure 2:
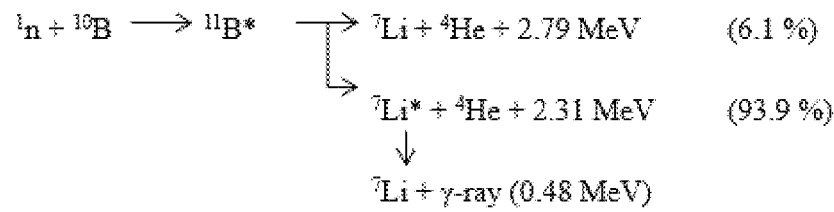
FIG. 2 is a nuclear reaction formula of $^{10}B$ (n,α) $^7Li$ neutron capture.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

The following description of the preferred embodiments is merely exemplary in nature and is in no way intended to limit the invention, its application, or uses.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components comprise, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7Li$ (p, n) $^7Be$ and $^9Be$ (p, n) $^9B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides the above-mentioned.

Requirements for the heat removal system differ as the selected nuclear reactions. $^7Li$ (p, n) $^7Be$ asks for more than $^9Be$ (p, n) $^9B$ does because of low melting point and poor thermal conductivity coefficient of the metal (lithium) target. In these embodiments of the present disclosure is $^7Li$ (p, n) $^7Be$.

No matter BNCT neutron sources are from the nuclear reactor or the nuclear reactions between the accelerator charged particles and the target, only mixed radiation fields are produced, that is, beams comprise neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux>$1\times10^9$ n/cm$^2$s
Fast neutron contamination<$2\times10^{-13}$ Gy-cm$^2$/n
Photon contamination<$2\times10^{-13}$ Gy-cm$^2$/n
Thermal to epithermal neutron flux ratio<0.05
Epithermal neutron current to flux ratio>0.7

Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than $2*10^{-13}$ Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$ Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

The prosthesis beam quality factors are deduced by virtue of the dose distribution in the tissue obtained by the prosthesis according to a dose-depth curve of the normal tissue and the tumors. The three parameters as follows may be used for comparing different neutron beam therapy effects.

1. Advantage Depth

Tumor dose is equal to the depth of the maximum dose of the normal tissue. Dose of the tumor cells at a position behind the depth is less than the maximum dose of the normal tissue, that is, boron neutron capture loses its advantages. The advantage depth indicates penetrability of neutron beams. Calculated in cm, the larger the advantage depth is, the larger the treatable tumor depth is.

2. Advantage Depth Dose Rate

The advantage depth dose rate is the tumor dose rate of the advantage depth and also equal to the maximum dose rate of the normal tissue. It may have effects on length of the therapy time as the total dose on the normal tissue is a factor capable of influencing the total dose given to the tumors. The higher it is, the shorter the irradiation time for giving a certain dose on the tumors is, calculated by cGy/mA-min.

3. Advantage Ratio

The average dose ratio received by the tumors and the normal tissue from the brain surface to the advantage depth is called as advantage ratio. The average ratio may be calculated using dose-depth curvilinear integral. The higher the advantage ratio is, the better the therapy effect of the neutron beams is.

To provide comparison reference to design of the beam shaping assembly, we also provide the following parameters for evaluating expression advantages and disadvantages of the neutron beams in the embodiments of the present disclosure except the air beam quality factors of IAEA and the abovementioned parameters.

1. Irradiation time<=30 min (proton current for accelerator is 10 mA)
2. 30.0RBE-Gy treatable depth>=7 cm
3. The maximum tumor dose>=60.0RBE-Gy
4. The maximum dose of normal brain tissue<=12.5RBE-Gy
5. The maximum skin dose<=11.0RBE-Gy Note: RBE stands for relative biological effectiveness. Since photons and neutrons express different biological effectiveness, the dose above should be multiplied with RBE of different tissues to obtain equivalent dose.

Figure 3:
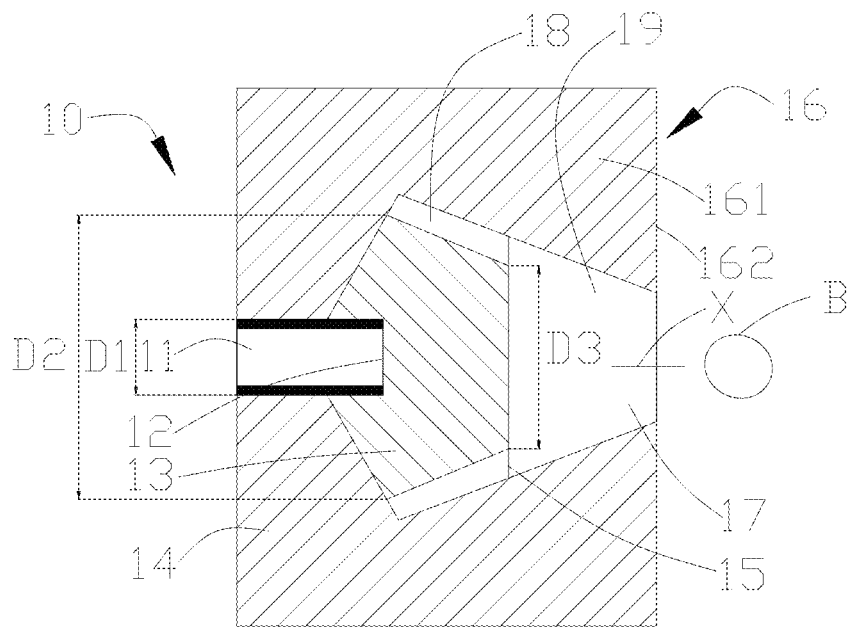
FIG. 3 is a schematic view of the beam shaping assembly for neutron capture therapy in the first embodiment of the present disclosure, wherein a gap channel is arranged between the moderator and the reflector.

In order to improve flux and quality of neutron sources, the embodiments of the present disclosure provides improvement of a beam shaping assembly for neutron capture therapy, preferably, improvement of a beam shaping assembly for AB-BNCT. As shown in FIG. 3, the beam shaping assembly 10 for neutron capture therapy in the first embodiment of the present disclosure comprises a beam inlet 11, a target 12, a moderator 13 adjacent to the target 12, a reflector 14 surrounding the moderator 13, a thermal neutron absorber 15 adjacent to the moderator 13, a radiation shield 16 and a beam outlet 17, wherein the radiation shield 16 is set inside the beam shaping assembly 10. The target 12 has nuclear reaction with an incident proton beam from the beam inlet 11 to produce neutrons; the neutrons form a neutron beam, the neutron beam defines a main axis X, and the neutrons are moderated by the moderator 13 to epithermal neutron energies, and the reflector 14 leads the neutrons deviated from the main axis X back to enhance epithermal neutron beam intensity; a gap channel 18 is placed between the moderator 13 and the reflector 14 so as to increase the epithermal neutron flux; the thermal neutron absorber 15 is used for absorbing thermal neutrons so as to avoid overdosing in superficial normal tissue during therapy; the radiation shield 16 is used for shielding the leaking neutrons and photons so as to reduce dose of a normal tissue not exposed to irradiation.

AB-BNCT accelerates a proton beam using an accelerator. Preferably, the target 12 is made of a metal material, and the proton beam is accelerated enough to overcome coulomb repulsion energy of a target atomic nucleus and has $^7$Li (p, n) $^7$Be reaction with the target 12 to produce neutrons. The beam shaping assembly 10 moderates the neutrons into epithermal neutron energies and reduces the quantity of thermal neutrons and fast neutrons; the moderator 13 is made of a material having a cross section for principally acting with fast neutrons but hardly acting with epithermal neutrons. Preferably, the moderator 13 is made of at least one of $D_2O$, $AlF_3$, Fluental™, $CaF_2$, $Li_2CO_3$, $MgF_2$ and $Al_2O_3$. The reflector 14 is made of a material having high neutron reflection ability, and is made of at least one of Pb or Ni preferably. The thermal neutron absorber 15 is made of a material having a cross section for acting with thermal neutrons and is made of $^6$Li preferably. An air passage 19 is placed between the thermal neutron absorber 15 and the beam outlet 17. The radiation shield 16 comprises a photon shield 161 and a neutron shield 162, and comprises a photon shield 161 made of plumbum (Pb) and a neutron shield 162 made of polyethylene (PE) preferably.

An outer surface of the moderator 13 includes the first tapered section and a second tapered section adjoining to the first tapered section, and a tapering direction of the first tapered section is opposite to a tapering direction of the second tapered section as shown in FIG. 3, the left side of the out surface of the moderator 13 is shaped in a first tapered section tapering gradually towards the left side, the right side of the out surface of the moderator 13 is shaped in a second tapered section tapering gradually towards the right side, and the two tapered sections connect to each other. Preferably, the left side of the out surface of the moderator 13 is shaped in a cone tapering towards the left side, and the right side may also be in other shapes adjacent to the cone, such as cylinder. The reflector 14 tightly surrounds the moderator 13, and a gap channel 18 is placed between the moderator 13 and the reflector 14. The so-called gap channel 18 is an empty area unfilled by solid materials and allowing neutron beams to pass easily. The gap channel 18 may be an air or vacuum passage. The thermal neutron absorber 15 arranged in the immediate vicinity of the moderator 13 is made of a thin $^6$Li material layer, the photon shield 161 made of Pb in the radiation shield 16 may be integrated with or separated from the reflector 14, the neutron shield 162 made of PE in the radiation shield 16 may be arranged near the beam outlet 17. An air passage 19 is placed between the thermal neutron absorber 15 and the beam outlet 17, in this area, neutrons deviated from the main axis X may be kept leading back to enhance epithermal neutron beam intensity. A prosthesis B is arranged at a position about 1 cm away from the beam outlet 17. Well known by those skilled in the art, the photon shield 161 may be made of other materials for shielding photons; the neutron shield 162 also may be made of other materials or arranged in other places for shielding leaking neutrons.

Figure 4:
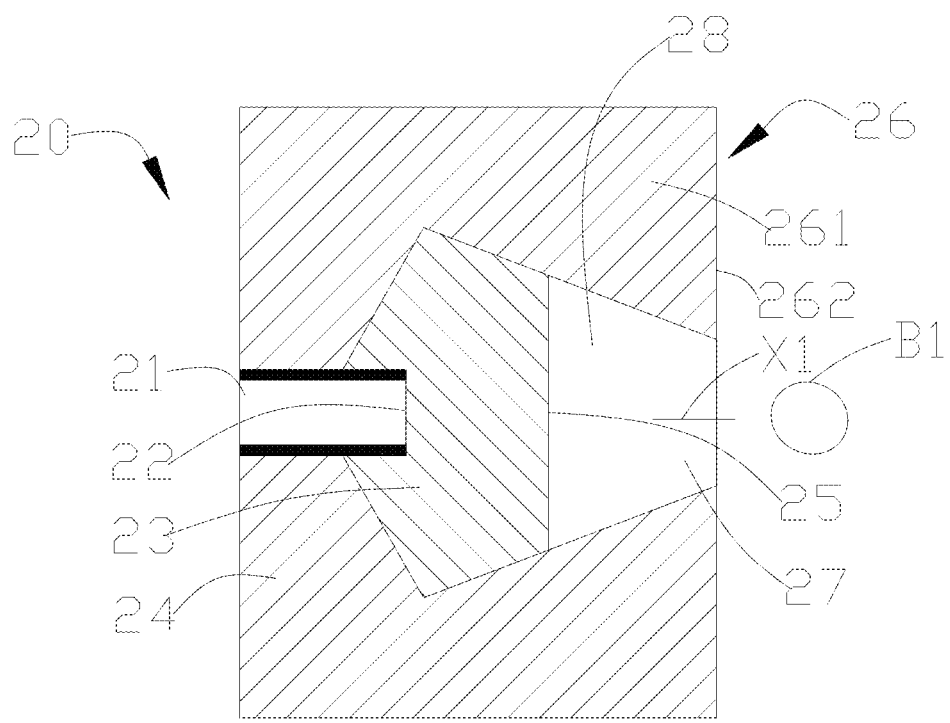
FIG. 4 is a schematic view of the beam shaping assembly for neutron capture therapy in the second embodiment of the present disclosure, wherein the outer surface of the moderator includes the first tapered section and a second tapered section adjoining to the first tapered section, and a tapering direction of the first tapered section is opposite to a tapering direction of the second tapered section, and the gap channel in the first embodiment is filled with materials of the moderator.
Figure 5:
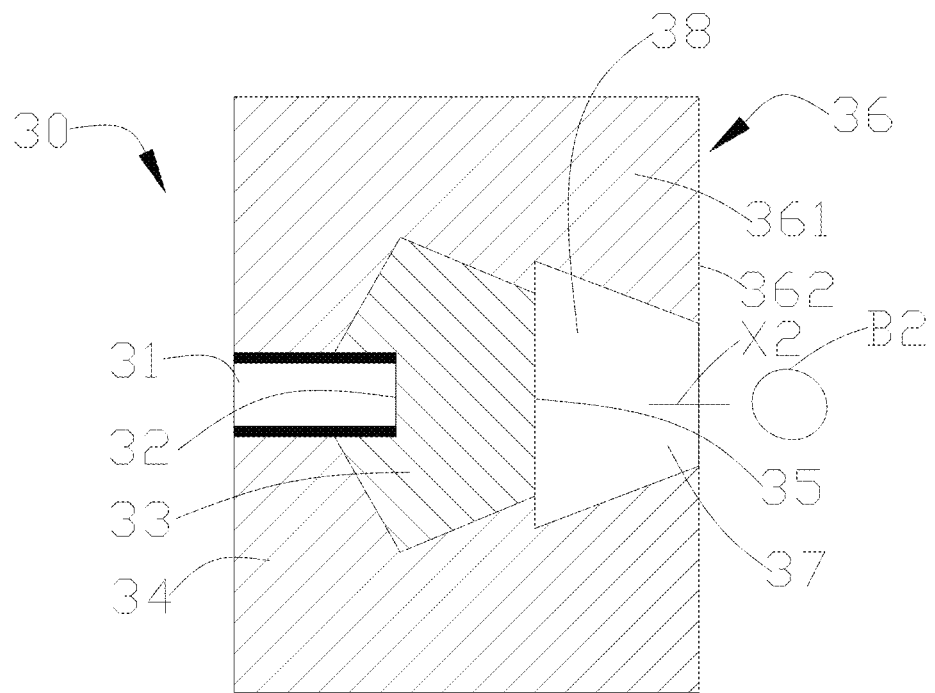
FIG. 5 is a schematic view of the beam shaping assembly for neutron capture therapy in the third embodiment of the present disclosure, wherein the outer surface of the moderator includes the first tapered section and a second tapered section adjoining to the first tapered section, and a tapering direction of the first tapered section is opposite to a tapering direction of the second tapered section, and the gap channel in the first embodiment is filled with materials of the reflector.

For comparing difference between the beam shaping assemblies with and without the gap channel, referring to FIGS. 4 and 5, the gap channel filled with the moderator in the second embodiment and the one filled with the reflector in the third embodiment are shown. Referring to FIG. 4 first, the beam shaping assembly 20 comprises a beam inlet 21, a target 22, a moderator 23 adjoining to the target 22, a reflector 24 surrounding the moderator 23, a thermal neutron absorber 25 adjacent to the moderator 23, a radiation shield 26 and a beam outlet 27, wherein the radiation shield 26 is set in the beam shaping assembly 20. The target 22 has nuclear reaction with an incident photon beam from the beam inlet 21 to produce neutrons, the neutrons form a neutron beam, the neutron beam defines a main axis X1, the neutrons are moderated by the moderator 23 to epithermal neutron energies, and the reflector 24 leads the neutrons deviated from the main axis X1 back to enhance the epithermal neutron beam intensity. An outer surface of the moderator 23 includes the first tapered section and a second tapered section adjoining to the first tapered section, and a tapering direction of the first tapered section is opposite to a tapering direction of the second tapered section as shown in FIG. 4, the left side of the out surface of the moderator 23 is shaped in a first tapered section tapering gradually towards the left side, the right side of the out surface of the moderator 23 is shaped in a second tapered section tapering gradually towards the right side, and the two tapered sections connect to each other. The thermal neutron absorber 25 is used for absorbing thermal neutrons so as to avoid overdosing in superficial normal tissue during therapy; the radiation shield 26 is used for shielding leaking neutrons and photons so as to reduce dose of the normal tissue not exposed to irradiation.

Preferably, the target 22, the moderator 23, the reflector 24, the thermal neutron absorber 25 and the radiation shield 26 in the second embodiment may be same as those in the first embodiment, wherein the radiation shield 26 comprises a photon shield 261 made of plumbum (Pb) and a neutron shield 262 made of polyethylene (PE), and the neutron shield 262 may be arranged at the beam outlet 27. An air passage 28 is placed between the thermal neutron absorber 25 and the beam outlet 27. A prosthesis B1 is arranged at a position about 1 cm away from the beam outlet 27.

Referring to FIG. 5, the beam shaping assembly 30 comprises a beam inlet 31, a target 32, a moderator 33 adjoining to the target 32, a reflector 34 surrounding the moderator 33, a thermal neutron absorber 35 adjoining to the moderator 33, a radiation shield 36 and a beam outlet 37, wherein the radiation shield 36 is set in the beam shaping assembly 30. The target 32 has nuclear reaction with an incident photon beam from the beam inlet 31 to produce neutrons, the neutrons form a neutron beam, the neutron beam defines a main axis X2, the neutrons are moderated by the moderator 33 to epithermal neutron energies, and the reflector 34 leads the neutrons deviated from the main axis X2 back to enhance the epithermal neutron beam intensity. An outer surface of the moderator 33 includes the first tapered section and a second tapered section adjoining to the first tapered section, and a tapering direction of the first tapered section is opposite to a tapering direction of the second tapered section as shown in FIG. 5, the left side of the out surface of the moderator 33 is shaped in a first tapered section tapering gradually towards the left side, the right side of the out surface of the moderator 33 is shaped in a second tapered section tapering gradually towards the right side, and the two tapered sections connect to each other. The thermal neutron absorber 35 is used for absorbing thermal neutrons so as to avoid overdosing in superficial normal tissue during therapy; the radiation shield 36 is used for shielding leaking neutrons and photons so as to reduce dose of the normal tissue not exposed to irradiation.

Preferably, the target 32, the moderator 33, the reflector 34, the thermal neutron absorber 35 and the radiation shield 36 in the third embodiment may be same as those in the first embodiment, wherein the radiation shield 36 comprises a photon shield 361 made of plumbum (Pb) and a neutron shield 362 made of polyethylene (PE), and the neutron shield 362 may be arranged at the beam outlet 37. An air passage 38 is placed between the thermal neutron absorber 35 and the beam outlet 37. A prosthesis B2 is arranged at a position about 1 cm away from the beam outlet 37.

The followings are analog computation of the three embodiments by MCNP software (a common-use software package developed by LosAlamos National Laboratory of the United States for computing neutrons, photons, charged particles or transporting coupled neutrons/photons/charged particles in 3D complicated geometric structures).

Among them, Table 1 as follow shows performances of air beam quality factors in the three different embodiments (each item in the table is calculated in the same unit above, so not repeat here and similarly hereinafter):

TABLE 1

Air Beam Quality Factors

| Air beam quality factors | Moderator-filled gap channel | Reflector-filled gap channel | Gap channel |
|---|---|---|---|
| Epithermal neutron flux | 1.35E+09 | 1.38E+09 | 1.42E+09 |
| Fast neutron contamination | 2.35E−13 | 2.58E−13 | 2.83E−13 |
| Photon contamination | 1.22E−13 | 8.92E−14 | 8.02E−14 |
| Thermal to epithermal neutron flux ratio | 0.03 | 0.02 | 0.02 |
| Epithermal neutron current to flux ratio | 0.64 | 0.64 | 0.64 |

Table 2 shows dose performance in the three embodiments:

TABLE 2

Dose Performance

| Dose Performance | Moderator-filled gap channel | Reflector-filled gap channel | Gap channel |
|---|---|---|---|
| Advantage depth | 10.9 | 10.9 | 11.0 |
| Advantage depth dose rate | 4.47 | 4.60 | 4.78 |
| Advantage rate | 5.66 | 5.69 | 5.68 |

Table 3 shows analog numerals of parameters for evaluating neutron beam dose performance in the three embodiments:

TABLE 3

Parameters for Evaluating Neutron Beam Dose Performance

| Parameters | Moderator-filled gap channel | Reflector-filled gap channel | Gap channel |
|---|---|---|---|
| Irradiation time | 25.3 | 24.8 | 23.9 |
| 30.0RBE-Gy treatable depth | 7.7 | 7.7 | 7.7 |
| Maximum tumor dose | 68.5 | 69.1 | 68.8 |
| Maximum dose of normal brain tissue | 11.3 | 11.4 | 11.4 |
| Maximum skin dose | 11.0 | 11.0 | 11.0 |

Figure 6:
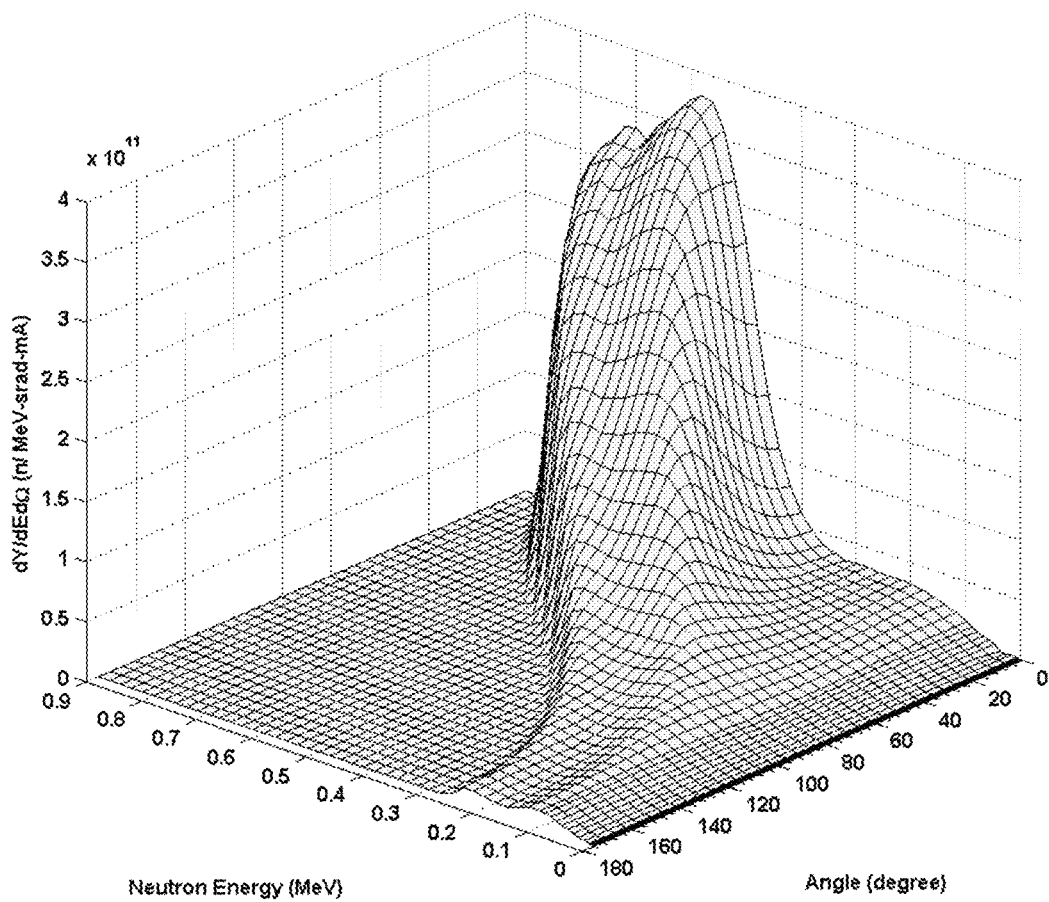
FIG. 6 is a double-differential graph of neutron yield from neutron energy and neutron angle.

Note:
it is observed from the three tables that the beam shaping assembly with the gap channel between the moderator and the reflector may supply neutron beams having best therapeutic effect Neutrons produced from the lithium target feature higher forward average energy. As shown in FIG. 6, the average neutron energy is about 478 keV at a neutron scattering angle between 0° and 30° of and is only about 290 keV between 30° and 180°. If forwardly travelling neutrons collide much with the moderator by changing the geometric shape of the beam shaping assembly, lateral neutrons may easily get to the beam outlet via less collision, so theoretically, neutron moderation may be best optimized and the epithermal neutron flux may be improved effectively. Now from geometric shapes of the beam shaping assembly we may evaluate influences on the epithermal neutron flux from different geometric shapes of the beam shaping assembly.

Figure 7:
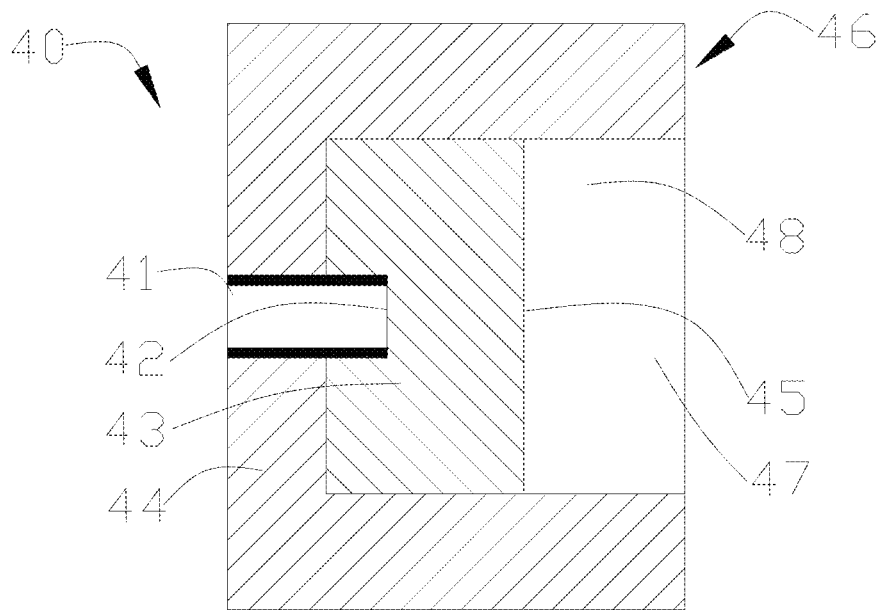
FIG. 7 is a schematic view of the beam shaping assembly for neutron capture therapy in the fourth embodiment of the present disclosure, wherein the moderator is cylindrical.

FIG. 7 is a view of a geometric shape of the beam shaping assembly in the fourth embodiment. The beam shaping assembly 40 comprises a beam inlet 41, a target 42, a moderator 43 adjoining to the target 42, a reflector 44 surrounding the moderator 43, a thermal neutron absorber 45 adjoining to the moderator 43, a radiation shield 46 and a beam outlet 47, wherein the radiation shield 46 is set in the bean shaping assembly 40. The target 42 has nuclear reaction with an incident photon beam from the beam inlet 41 to produce neutrons, the neutrons are moderated by the moderator 43 to epithermal neutron energies, and the reflector 44 leads the deviated neutrons back to enhance the epithermal neutron beam intensity. An out surface of the moderator 43 is columnar, preferably, cylindrical. The thermal neutron absorber 45 is used for absorbing thermal neutrons so as to avoid overdosing in superficial normal tissue during therapy; the radiation shield 46 is used for shielding leaking neutrons and photons so as to reduce dose of the normal tissue not exposed to irradiation, and an air passage 48 is placed between the thermal neutron absorber 45 and the beam outlet 47.

Figure 8:
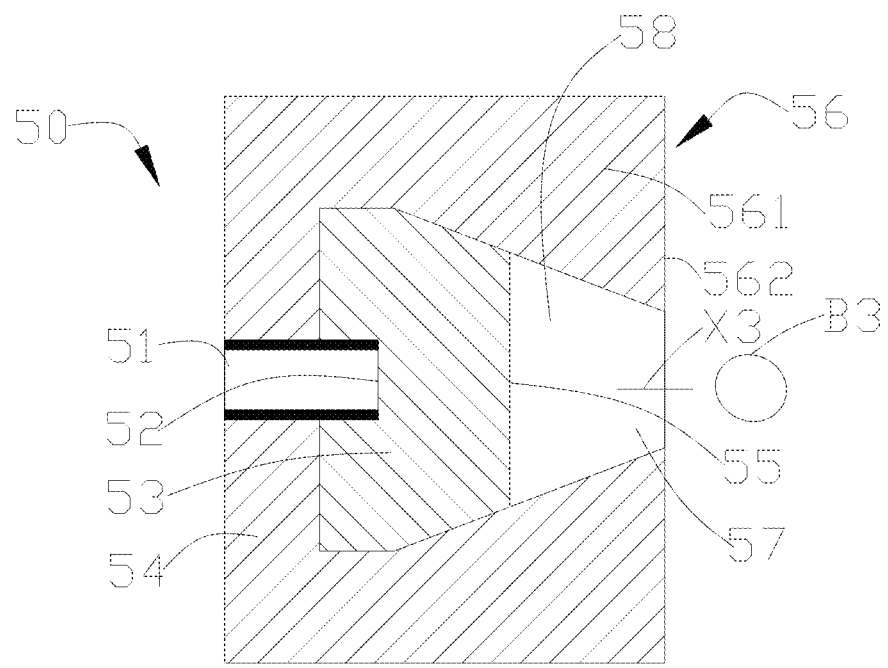
FIG. 8 is a schematic view of the beam shaping assembly for neutron capture therapy in the fifth embodiment of the present disclosure, wherein the outer surface of the moderator includes a cylindrical section and the first tapered section adjoining to the cylindrical section.

FIG. 8 is a view of a geometric shape of the beam shaping assembly in the fifth embodiment. The beam shaping assembly 50 comprises a beam inlet 51, a target 52, a moderator 53 adjoining to the target 52, a reflector 54 surrounding the moderator 53, a thermal neutron absorber 55 adjoining to the moderator 53, a radiation shield 56 and a beam outlet 57, wherein the radiation shield 56 is set in the beam shaping assembly 50. The target 52 has nuclear reaction with an incident photon beam from the beam inlet 51 to produce neutrons, the neutrons form a neutron beam, the neutron beam defines a main axis X3, the neutrons are moderated by the moderator 53 to epithermal neutron energies, and the reflector 54 leads the neutrons deviated from the main axis X3 back to enhance the epithermal neutron beam intensity. An out surface of the moderator 53 includes a cylindrical section and a tapered section adjoining to the cylindrical section, the left side of the out surface of the moderator 53 is shaped in a cylinder, the right side of the out surface of the moderator 53 is shaped in a cone tapering gradually from the right side, and the cylinder and the cone are adjacent to each other. The thermal neutron absorber 55 is used for absorbing thermal neutrons so as to avoid overdosing in superficial normal tissue during therapy; the radiation shield 56 is used for shielding leaking neutrons and photons so as to reduce dose of the normal tissue not exposed to irradiation.

Preferably, the target 52, the moderator 53, the reflector 54, the thermal neutron absorber 55 and the radiation shield 56 in the fifth embodiment may be same as those in the first embodiment, wherein the radiation shield 56 comprises a photon shield 561 made of plumbum (Pb) and a neutron shield 562 made of polyethylene (PE), and the neutron shield 562 may be arranged at the beam outlet 57. An air passage 58 is placed between the thermal neutron absorber 55 and the beam outlet 57. A prosthesis B3 is arranged at a position about 1 cm away from the beam outlet 57.

In the following, results of analog computation of the moderator with an out surface including two opposite tapered sections in the second embodiment, the cylindrical moderator in the fourth embodiment and the moderator with an out surface including a cylindrical section and a tapered section adjoining to the cylindrical section in the fifth embodiment by MCNP are shown.

Among them, Table 4 shows air beam quality factors in these three embodiments:

TABLE 4

Air Beam Quality Factors

| Air beam quality factors | Cylindrical section | A cylindrical section and a tapered section | Two opposite tapered sections |
|---|---|---|---|
| Epithermal neutron flux | 7.14E+08 | 1.29E+09 | 1.35E+09 |
| Fast neutron contamination | 2.67E−13 | 2.40E−13 | 2.35E−13 |
| Photon contamination | 1.72E−13 | 1.42E−13 | 1.22E−13 |
| Thermal to epithermal neutron flux ratio | 0.04 | 0.03 | 0.03 |
| Epithermal neutron current to flux ratio | 0.69 | 0.64 | 0.64 |

Table 5 shows dose performance in these three embodiments:

TABLE 5

Dose Peformance

| Dose Performance | Cylindrical section | A cylindrical section and a tapered section | Two opposite tapered sections |
|---|---|---|---|
| Advantage depth | 11.8 | 10.9 | 10.9 |
| Advantage depth dose rate | 2.95 | 4.28 | 4.47 |
| Advantage rate | 5.52 | 5.66 | 5.66 |

Table 6 shows analog numerals of parameters for evaluating neutron beam dose performance in these three embodiments:

TABLE 6

Parameters for Evaluating Neutron Beam Dose Performance

| Parameters | Cylindrical section | A cylindrical section and a tapered section | Two opposite tapered sections |
|---|---|---|---|
| Irradiation time (10 mA) | 40.7 | 26.1 | 25.3 |
| 30.0RBE-Gy treatable depth | 8.4 | 7.6 | 7.7 |
| Maximum tumor dose | 70.9 | 67.4 | 68.5 |
| Maximum dose of normal brain tissue | 12.0 | 11.2 | 11.3 |
| Maximum skin dose | 11.0 | 11.0 | 11.0 |

Note:
it is observed from these three tables that the out surface of the moderator may include at least one tapered section, and its neutron beams may achieve better therapeutic effect.

The term 'cylindrical' or 'cylindrical section' referred in the embodiment of the present disclosure is an element with the contour in a substantially unchanged trend from one side to the other side along the illustrated direction. One of contour lines may be a line segment, like a corresponding one of the cylinder, or may be a high-curvature arc approximate to the line segment, like a corresponding one of a sphere with high curvature. The integral surface of the contour may be continuously connected or not if the surface of the cylinder or the high-curvature sphere is provided with many protrusions and grooves.

The term 'tapered' or 'tapered section' referred in the embodiment of the present disclosure is an element with the contour in a tapering trend from one to the other side along the illustrated direction. One of contour lines may be a line segment, like a corresponding one of the cone, or may be an arc, like a corresponding one of the sphere, and the integral surface of the contour may be continuously connected or not if the surface of the cone shape or the spherical shape is provided with plenty of protrusions and grooves.

In an important aspect of source flux improvement, it is necessary to discuss the preparation of the material of the moderator, and the moderator 13 is further elaborated hereinafter with the first embodiment and FIG. 3 as an example.

The moderator 13 shows a double-taper structure in which the directions of the two tapered sections are completely opposite, the material of the moderator 13 is prepared from a material containing at least one of $AlF_3$, $CaF_2$ and $MgF_2$, and the moderator 13 has a first diameter D1 perpendicularly to the main axis X, a second diameter D2 perpendicularly to the main axis X and a third diameter D3 perpendicularly to the main axis X. An opening is arranged at the first diameter D1 so as to contain the target 12, and the second diameter D2 is arranged as the maximum size of the double-taper structure. For BNCT, in order to achieve an enough moderating effect, the first diameter D1 is 1 cm to 20 cm in length, the second diameter D2 is 30 cm to 100 cm in length, and the third diameter D3 is 1 cm to 50 cm in length; as a preference, the first diameter D1 is 10 cm in length, the second diameter D2 is 70 cm in length, and the third diameter D3 is 30 cm in length. In order to obtain the moderator 13 with such a large size, the density of its material is 80 to 100 percent of theoretical density, and the preparation of the following three types of moderator materials is provided.

1. Crystal Growing $MgF_2$ is taken as an example first, and please further refer to invention patent application publication No. CN102925963A, which is completely introduced as a reference for crystal growing preparation herein. As a crystal growing method, usually a seed crystal and $MgF_2$-containing powders are put into a crucible, and an $MgF_2$ monocrystal is grown in a certain way.

It should be especially noted that the so-called "monocrystal" here means a single crystal which is grown to form once, rather than a single crystalline grain (that is, there is only one crystalline form and only one crystalline grain is contained, and molecules and atoms in the crystalline grain are all arranged regularly). It can be better understood that such a single crystalline grain is different from multiple crystalline grains (that is, the sizes and shapes of the crystalline grains are different, moreover, orientations are in disorder as well, there are no distinct shapes, and the crystalline grains do not also show anisotropy). The definition about "monocrystal" hereinafter is the same as here.

Through research, $PbF_4$, $AlF_3$, $CaF_2$ and $Al_2O_3$ can also be prepared in a similar way.

2. Powder Sintering

The powders or powder compacts of $MgF_2$, $AlF_3$ or $CaF_2$ is further combined, the powder grains will undergo physical and chemical processes, such as mutual flowing, diffusion, dissolution and recrystallization, in the process of sintering, consequently, the powders is further compacted, and part or all of voids therein are eliminated. There can be a lot of sintering methods, such as solid-phase sintering, i.e., sintering temperature is lower than the melting point of each component in the powder; liquid-phase sintering, i.e., if there are two or more types of components in the powder compact, sintering may take place above the melting point of a certain component, so a small amount of liquid phase will appear in the powder compact during sintering; hot-press sintering, i.e., during sintering, pressure is applied to the powder so as to promote the process of powder compaction, and hot pressing is a technological process which combines the shaping and sintering of powder together to directly obtain a product; and spark plasma sintering, i.e. a rapid sintering technique, i.e., by applying ON-OFF direct-current pulse voltage generated by a special power controller to a powdery test sample, a sintering promotion effect caused by a spark discharge phenomenon (the instantaneous generation of high-temperature plasma) generated in powder at the initial stage of pulse discharge can effectively utilized, besides the common sintering promotion effect (discharge impact pressure and Joule heating) engendered by discharge processing, to implement compaction through an instantaneous high temperature field. The powder sintering device turns the material of the moderator into blocks from the powders or powder compacts through a powder sintering process.

As known well by those skilled in the art, other sintering methods can also implement the preparation of at least one or a mixture of more of $MgF_2$, $AlF_3$ and $CaF_2$ as the material of the moderator. As a preference, hot-press sintering and spark plasma sintering are taken as embodiments of powder sintering hereinafter.

$MgF_2$ powder or mixed powder in which $^6LiF$ accounting for 0.1 to 5 percent by weight of $MgF_2$ powder is added in $MgF_2$ is then taken as an example for the introduction of powder sintering, and preferably, the mixed powder in which $^6LiF$ accounting for 0.1 to 5 percent of the percentage by weight of the $MgF_2$ powder is added in $MgF_2$ is taken as an example for the introduction of powder sintering.

The moderator plays a vital role in the beam shaping assembly, undertaking great responsibility for neutron moderation, and it needs to reduce fast neutron intensity as much as possible without excessively moderating neutrons into thermal neutrons, and, on the other hand, must also reduce y rays derived in the process of moderation. A research indicates that the intensity of y rays can be effectively decreased by evenly adding a small amount of $^6Li$-containing material into the moderator, and although neutron intensity would be slightly decreased, original beam quality is still kept. In a further research, $^6LiF$ powder accounting for 0.1 to 5 percent by weight of $MgF_2$ powder is mixed into the $MgF_2$ powder, and compared with the pure $MgF_2$ powder without the $^6LiF$ powder, the mixed powder can more effectively absorb thermal neutrons and effectively inhibit y rays.

When the $^6Li$-containing material accounting for 0.1 to 5 percent by weight of the $MgF_2$ powder is mixed into the $MgF_2$ powder to form a moderator material, it is known well to those skilled in the art that the $^6Li$-containing material can be of any physical form which can be easily mixed with the $MgF_2$ powder, for example, the $^6Li$-containing material can be liquid or powder. The $^6Li$-containing material can be any compound which can be easily mixed with the $MgF_2$ powder, and the $^6Li$-containing material can be $^6LiF$ or $^6Li_2CO_3$. As a preference, the $MgF_2$ powder and the $^6LiF$ powders or powder compacts accounting for 0.1 to 5 percent by weight of the $MgF_2$ powder are further combined, the powder grains will undergo physical and chemical processes, such as mutual flowing, diffusion, dissolution and recrystallization, in the process of sintering, consequently, the powder is further compacted, and part or all of voids therein are eliminated. There can be a lot of sintering methods, such as solid-phase sintering, i.e., sintering temperature is lower than the melting point of each component in the powder; liquid-phase sintering, i.e., if there are two or more types of components in the powder compact, sintering may take place above the melting point of a certain component, so a small amount of liquid phase will appear in the powder compact during sintering; hot-press sintering, i.e., during sintering, pressure is applied to the powder so as to promote the process of powder compaction, and hot pressing is a technological process which combines the shaping and sintering of powder together to directly obtain a product; and spark plasma sintering, i.e. a rapid sintering technique, i.e., by applying ON-OFF direct-current pulse voltage generated by a special power controller on a powdery test sample, a sintering promotion effect caused by a spark discharge phenomenon (the instantaneous generation of high-temperature plasma) generated in powder at the initial stage of pulse discharge can be effectively utilized, besides the common sintering promotion effect (discharge impact pressure and Joule heating) engendered by discharge processing, to implement compaction through an instantaneous high temperature field. The powder sintering device turns the material of the moderator into a block from the powders or powder compacts through a powder sintering process.

As known well by those skilled in the art, other sintering methods can also implement the preparation of the material of the moderator by adding $^6LiF$ powder into at least one or a mixture of $MgF_2$, $AlF_3$, $CaF_2$ and $PbF_4$. As a preference, hot-press sintering and spark plasma sintering are taken as embodiments of powder sintering hereinafter.

2.1 Spark Plasma Sintering

Spark plasma sintering integrates plasma activation, hot pressing and resistance heating into a whole, temperature rise is rapid, sintering time is short, and sintering temperature is low, crystalline grains are uniform, the control of the microstructure of a sinter is benefited, the compactness of the obtained material is high, and moreover, spark plasma sintering has the advantages of simplicity in operation, high repeatability, high safety and reliability, space saving, energy saving, low cost, etc. Because spark plasma sintering applies strong pulse current between powder grains, electrical field-induced anodes and cathodes exist between the powder grains, discharge takes place between the grains under the effect of the pulse current, exciting plasma, high-energy particles generated by discharge impact the contacted portions of the grains, so that the substance produces an evaporation effect, playing a purifying and activating role, electrical energy is stored in the dielectric layers of the clusters of grains, and the dielectric layers discharge electricity intermittently and rapidly. Since the pulse current exists in the powders or powder compacts and occurs instantaneously and intermittently at high frequency, both discharge heat generated by the uncontacted portions of the powder grains and Joule heat generated by the contacted portions of the powder grains can greatly promote the diffusion of powder grain atoms, the diffusion coefficient is much greater than that under the normal hot pressing condition, and thereby the rapidness of powder sintering is achieved. Moreover, because of the addition of the pulse current, both the discharging portions and Joule heating portions in the powder will move rapidly, so that the sintering of the powders or powder compacts can be uniform. In the process of spark plasma sintering, as discharge occurs between the grains, local high temperature which is as high as thousands of degrees Celsius to ten thousand degrees Celsius is generated instantaneously, causing evaporation and melting of the surfaces of the grains, as a result, necks are formed at the contact points of the grains, and because heat is immediately transferred from the heating center to the surfaces of the grains and diffused in all directions, the necks are cooled rapidly, leading to vapor pressure lower than that of the other portions. The gas-phase substance is agglomerated on the necks to form evaporation-solidification transition higher than that in ordinary sintering methods, which is another important characteristic of the spark plasma sintering process. Because pulse current heating and vertical unidirectional pressure act on the crystalline grain, both bulk diffusion and grain boundary diffusion are enhanced, the process of sintering compaction is accelerated, and therefore a high-quality sinter can be obtained with low temperature in a short time. The spark plasma sintering process can be regarded as a result of the comprehensive effect of grain discharge, conductive heating and pressing.

Figure 9:
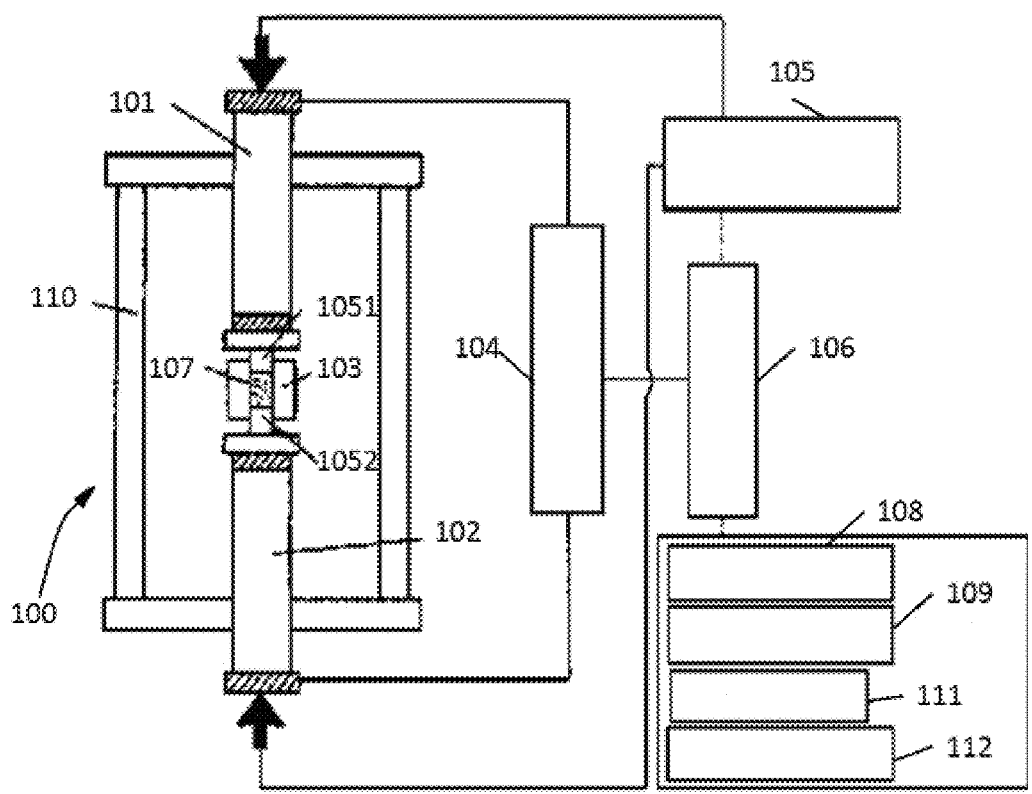
FIG. 9 is a schematic view of a preparation device for a moderator material in one embodiment of the present disclosure, wherein the preparation device is a spark plasma sintering device.

Refer to FIG. 9, it discloses a schematic view of a spark plasma sintering device. The spark plasma sintering device 100 includes a first electrode 101, a second electrode 102, a conductive mold 103 arranged between the first electrode 101 and the second electrode 102, a pulse current generator 104 for providing pulse current for the mold 103, a pressing assembly 105 with pressing members 1051, 1052 for pressing the powders or pawder compacts, and a controller 106 for controlling the pulse current generator 104 and the pressing assembly 105, at least one of the first electrode 101 and the second electrode 102 can be moved, and at least one of the pressing members 1051, 1052 can be moved; as a preference, the first electrode 101 and the pressing part 1051 are fixed, the second electrode 102 and the pressing part 1052 can be moved, and thereby powders or powder compacts 107 loaded in the mold 103 can be pressed. As a preference, the conductive mold 103 is of lead or graphite. The spark plasma sintering device 100 further includes a position measurement system 108 for measuring the position of the pressing assembly 105, an atmosphere control system 109 for controlling atmosphere in the mold 103, a water cooling system 111 for controlling a water-cooling vacuum chamber 110 to carry out cooling, and a temperature measurement system 112 for measuring temperature in the spark plasma sintering device 100. Pulse current is applied to the mold 103 and the powders or powder compacts 107; besides providing discharge impact pressure and Joule heat for sintering, a sintering promotion effect caused by a spark discharge phenomenon (the instantaneous generation of high-temperature plasma) generated in powder at the initial stage of pulse discharge is further utilized to implement rapid sintering through an instantaneous high temperature field, so that the powders or powder compacts 107 are turned into blocks from the powder state, and the so-called blocks are integrally formed without needing, for example, putting together monocrystals by steps, such as grinding or polishing, to match the dimensions of the moderator, like the crystal growing method.

The spark plasma sintering device 100 utilizes direct-current pulse current to be directly electrified for sintering and pressing, and controls the rate of temperature rise and sintering temperature by regulating the magnitude of the direct-current pulse current through the controller 106. The whole sintering process can be carried out under a vacuum environment, or can be carried out in protective atmosphere, such as oxygen or hydrogen.

Under oxygen atmosphere, because oxygen is adsorbed by the surface of the sinter or chemical reaction occurs, a cation vacancy type non-stoichiometric compound is formed on the surface of the crystal, cation vacancies are increased, meanwhile, oxygen in closed apertures can directly get into the crystal lattice, and is diffused along the surface like oxygen ion vacancies, and diffusion and sintering are accelerated. When sintering is controlled by cation diffusion, oxidizing atmosphere or oxygen partial pressure is high and favorable for the formation of the cation vacancies, promoting sintering; and when sintering is controlled by anion diffusion, reducing atmosphere or low oxygen partial pressure will lead to the generation of oxygen ion vacancies and promote sintering.

When a sample is sintered under hydrogen atmosphere, as the radius of the hydrogen atom is very small, hydrogen is easy to diffuse and beneficial to elimination of closed apertures, and when a type of material, such as alumina, is sintered under the hydrogen atmosphere, a sinter sample which approximates theoretical density can be obtained.

Sintering temperature is one of key parameters in the process of plasma rapid sintering. The determination of a sintering temperature must take the phase transformation of the sinter sample under high temperature, the growth rate of a crystalline grain, the requirement on the quality of the sample and the requirement on the density of the sample into consideration. In general, as sintering temperature rises, the overall compactness of a test sample tends to increase, this indicates that sintering temperature has remarkable influence on the compactness degree of the sample, and the higher sintering temperature is, the higher the speed of substance transmission is in the process of sintering and the easier the sample is to compact.

However, the higher temperature is, the higher the growth rate of a crystalline grain is and the poorer its mechanical properties are. When temperature is too low, the compactness of the sample is very low, and quality cannot meet a requirement. Due to the contradiction between temperature and crystalline grain size, an appropriate parameter is required in respect of temperature choice.

Normally, prolonging temperature keeping time under sintering temperature will promote the completion of sintering to different degrees and perfect the microstructure of the sample, which is more obvious for sintering for a viscose flow mechanism while having less influence on sintering for bulk diffusion and surface diffusion mechanism. In the process of sintering, normally, when temperature is kept for only one minute, the density of the sample reaches not less than 96.5 percent of theoretical density; as temperature keeping time extends, the compactness of the sample increases, but the variation range is not broad, and this indicates that although the temperature keeping time has certain influence on the compactness of the sample, the effect of action is not remarkable. However, if the temperature keeping time under the sintering temperature is prolonged unreasonably, the crystalline grain will rapidly grow within the time, intensifying secondary recrystallization, which is adverse to a requirement on the properties of the sample, and if the time is too short, it will cause a decrease in the compactness of the sample, so it is necessary to choose an appropriate temperature keeping time.

With an increase in the rate of temperature rise, the sample reaches a required temperature within a short time, the growth time of the crystalline grain will be greatly shortened, and this not only helps to inhibit the crystalline grain from growing up, so that a fine-grained ceramic with uniform size can be obtained, but also can save time and energy and increase the utilization rate of the sintering device. However, due to the limitation of the device, an overhigh rate of temperature rise will cause a destructive effect on the device. For this reason, the rate of temperature rise should be increased as much as possible within an allowable range. Nevertheless, it is reflected in measured experimental data that different from sintering temperature and temperature keeping time, the influence of the rate of temperature rise on sample compactness shows an opposite result, that is, as the rate of temperature rise increases, sample compactness shows a tendency of coarsening and gradually decreasing. Some scholars have suggested that this is because the increase of the rate of temperature rise near sintering temperature is equivalent to the shortening of temperature keeping time, so sample compactness will decrease to a certain degree. In an actual high-temperature sintering process, the temperature rise process is normally divided into three stages, i.e. a stage from room temperature to about 600° C., a stage from 600° C. to about 900° C. and a stage from 900° C. to a sintering temperature: the first stage is a preparation stage, and the rate of temperature rise is relatively slow; the second stage is a controllable rapid temperature rise stage, and the rate of temperature rise is normally controlled at 100 to 500 (° C./min); the third stage is a buffering stage of temperature rise, temperature is slowly increased to the sintering temperature at this stage, the temperature keeping time is normally one to seven minutes, a sinter is cooled along with the furnace after temperature keeping, and the cooling rate can reach 300° C./min.

After sufficient discharge treatment, powders are immediately pressed to be shaped and sintered. The sintered material is severely plastically deformed under the combined action of resistance Joule heat and pressure, applying forming pressure can help to enhance the contact between the powder grains, enlarge sintering area, exhaust residual gas in the sintered powder and increase the strength, density and surface smoothness of a product. The magnitude of forming pressure is normally determined according to the compactness of the sintered powder and requirements on the properties of the sintered material, such as density and strength, and is normally within a range from 15 MPa to 30 MPa, and sometimes, may be as high as 50 MPa or even higher. Usually, the higher forming pressure is, the density of the sintered material is. The duration of pressure application will also greatly affect the density of the sintered material, and depending on varieties of sintered materials, powder grain sizes and geometrical dimensions of the sintered materials, appropriate pressure application time may be different, and needs to be determined by experiments. An experiment proves that the duration of pressure application is equal to or slightly greater than discharge time, and this is a necessary condition to obtain a sintered material with the highest density. It is easy to understand from a sintering and solid-phase reaction mechanism that the higher pressure is, the more tightly grains in a sample heap, mutual contact points and contact areas are enlarged, and sintering is accelerated. Thus, the sample can obtain better compactness, moreover, the crystalline grain can be effectively inhibited from growing up, and sintering temperature can be decreased. Therefore, chosen pressure is normally 30 Mpa to 50 MPa. Nevertheless, a research indicates that during sintering, when external pressure is 30 MPa and 50 MPa, the difference between the compactnesses of the sample is not great, and this suggests that the phenomenon that compactness increases along with pressure is only obvious within a certain range.

Compared with conventional sintering techniques, spark plasma sintering has the following advantages: sintering speed is high; material microstructures are improved, and the properties of materials are increased.

As known well by those skilled in the art, the mold can be produced by using other conductive materials, the spark plasma sintering device can also be so arranged that both electrodes are fixed, while only at least one pressing member can move.

The main process flow of spark plasma sintering is divided into four stages in total. First stage: initial pressure is applied to a powder sample to make the powder grains be in sufficient contact with one another, so that uniform and sufficient spark plasma can be generated in the powder sample later; Second stage: pulse current is applied, the contact points of the powder grains generate spark plasma under the effect of the pulse current, and the grain surfaces generate a slight heat releasing phenomenon due to activation; Third stage: a pulse power supply is switched off, resistance heating is carried out on the sample until the sample reaches a predetermined sintering temperature and the contraction of the sample is complete; Fourth stage: pressure is released. By reasonably controlling main technological parameters, such as initial pressure, sintering time, forming time, pressure application duration, sintering temperature and the rate of temperature rise, a material with good comprehensive properties can be obtained.

Due to a bridging effect between the powder grains, they cannot be in sufficient contact normally, so, in order to generate uniform and sufficient-discharge plasma in the sample during spark sintering and activate the grain surfaces to the max to accelerate the sintering compaction process, appropriate initial pressure needs to be applied to the sintered powders, so that the powder grains can be in sufficient contact. The magnitude of initial pressure may be different, depending on varieties of sintered powders and sizes and properties of sinters. If initial pressure is too low, the discharge phenomenon will be only limited to part of the powders, leading to the partial melting of the powders; if initial pressure is too high, discharge will be inhibited, and the sintering diffusion process will then be retarded. According to existing literature, in order to make discharge proceed continuously and sufficiently, the initial pressure should not exceed 10 MPa normally.

When a powder test sample with good spark sintering conductivity is used, because resistance heating is carried out simultaneously from the outside and inside of the sample, the sintering time is extremely short or even instantaneous, but the length of the sintering time should be different according to qualities, varieties and properties of powders, and is normally several seconds to several minutes; and when a large, difficult-to-melt metal powder material is sintered, the sintering time is even up to tens of minutes. Sintering time has great influence on the density of the product, and in order to make the compaction process proceed sufficiently, a certain sintering time needs to be guaranteed.

It is generally believed that rapid temperature rise in the process of spark plasma sintering is beneficial to the sintering of powders because it inhibits the non-compaction mechanism of the material and activates the compaction mechanism of the material, so increasing the rate of temperature rise can make the compaction degree of the sample increased.

As a preference, the spark plasma sintering process includes the following steps: filling the mold 103 with an appropriate amount of powders or powder compacts 107; moving the pressing assembly 105 to press the powders or powder compacts 107 in the mold 103; switching on, by utilizing the controller 106, the pulse current generator 104 to electrify the mold 103, so that plasma is generated and the surfaces of the powder grains are activated and heat; and sintering the powders or powder compacts 107 into blocks. The spark plasma sintering process further includes the following steps: the controller 106 controls the position measurement system 108 to ensure the normal operation of the position measurement system 108, the controller 106 controls the atmosphere control system 109 to ensure that atmosphere in the mold 103 is under the condition of normal operation, the controller 106 controls the water cooling system 111 to ensure that it is under the condition of normal operation, and the controller 106 controls the temperature measurement system 112 to ensure that temperature in the spark plasma sintering device 100 is under the condition of normal operation. The so-called normal operation means that the spark plasma sintering device does not generate visual, tactile or auditory warning signals perceivable by the human being, such as the shining of a warning indicator light, the sounding of the warning indicator light, warning indicator vibration and the like.

2.2 Hot-Press Sintering

Hot-press sintering is a sintering method in which dry powder is loaded into the mold, and is then pressed in a single-axis direction while being heated, so that forming and sintering are complete at the same time. The hot-press sintering technique is rich in production processes, and there are no unified specifications and standard for classification at present. According to current situation, the production processes can be divided into vacuum hot pressing, hot pressing under atmosphere, vibratory hot pressing, balanced hot pressing, hot isostatic pressing, reaction hot pressing and ultrahigh-pressure sintering. Since heating and pressing are carried out simultaneously in hot-press sintering, the powder is in a thermoplastic state, which is favorable for the proceeding of the contact diffusion and flowing mass transfer process of the grains, and therefore forming pressure is only one tenth of that in cold pressing; furthermore, sintering temperature can be decreased, sintering time can be shortened, and thereby the crystalline grain is inhibited from growing up, obtaining a product with a fine crystalline grain, high compactness and good mechanical and electrical properties.

Figure 10:
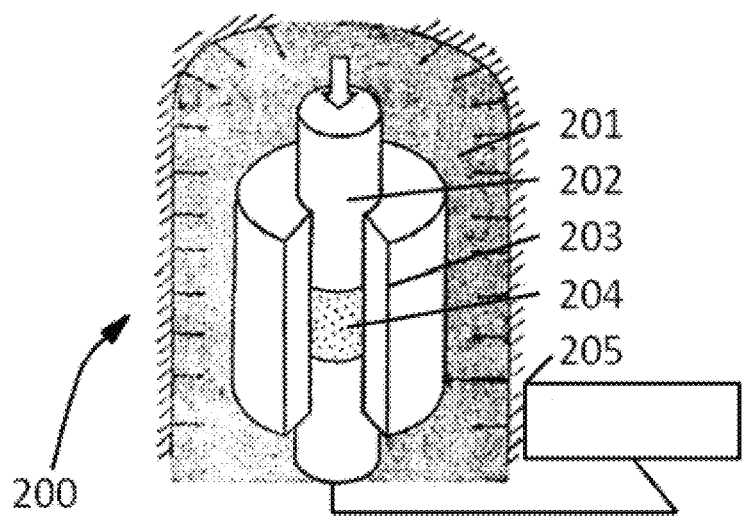
FIG. 10 is a schematic view of a preparation device for a moderator material in one embodiment of the present disclosure, wherein the preparation device is a hot-press sintering device.

In order to adopting the hot-press sintering process to prepare a moderator material, refer to FIG. 10, a hot-press sintering device 200 mainly includes a heating furnace 201, a pressing assembly 202 arranged in the heating furnace 201, a mold 203, powders or powder compacts 204 loaded in the mold 203, and a controller 205. The heating furnace 201 normally adopts electricity as a heat source, and a heating element is made of an SiC, MoSi or nichrome wire, a platinum wire, a molybdenum wire, etc. The pressing assembly 202 is required to be steady and slow in speed, constant in pressure keeping and flexible in pressure regulation, and normally, there are a lever type and a hydraulic type. According to the requirement of material properties, pressurized atmosphere can be air, as well as reducing atmosphere or inert atmosphere. The mold 203 is required to be high in strength, high temperature resistant, oxidation resistant and not sticking with a hot-pressed material, the thermal expansion coefficient of the mold 203 should be consistent with or approximate that of the hot-pressed material, and as a preference, a graphite mold is adopted in the present embodiment. The controller 205 ensures that the hot-press sintering device 200 is under the condition of normal operation. The so-called normal operation means that the spark plasma sintering device does not generate visual, tactile or auditory warning signals perceivable by the human being, such as the shining of a warning indicator light, the sounding of the warning indicator light, warning indicator vibration and the like.

Taking adopting the hot-press sintering process to prepare a target moderator from $MgF_2$ as an example, the production process flow generally includes the following steps: preparation of $MgF_2$ material—grinding and screening of material—transferring into mold—high-temperature sintering—high-temperature hot-press sintering—cooling and discharge—hot isostatic pressure—high-temperature sintering—cooling and discharge—grinding, polishing and bonding—finished product.

As a preference, the preceding powder treatment step and the succeeding treatment step for sintering completion are omitted here. The hot-press sintering process includes the following steps: filling the mold 203 with an appropriate amount of powders or powder compacts 204; switching on the hot-press furnace 201 to preset pressure and temperature parameters; moving the pressing assembly 202 to press the powders or powder compacts 204 in the mold 203; controlling, by the controller 205, the hot-press sintering device 200 to be under the condition of normal operation; and switching on power to sinter the powders or powder compacts 204 into blocks.

It needs to be further explained that the step "moving the pressing assembly 202 to press the powders or powder compacts 204 in the mold 203" in the hot-press sintering process can be prepressing or carried out as the power is switched on, that is, the step "moving the pressing assembly 202 to press the powders or powder compacts 204 in the mold 203" and the step "switching on power to sinter the powders or powder compacts 204 into blocks" are integrated.

Some parameters of crystal growing, spark plasma sintering and hot-press sintering are listed in the following table for comparison. As a material which more easily to be used for the moderator in the beam shaping assembly for neutron capture therapy disclosed in the present disclosure, a moderator material which is prepared by powder sintering is suggested to be used here, especially under the prerequisite of needing to produce a moderator with dimensions among which the maximum second diameter D2 is up to 100 cm, and see the specific description below.

TABLE 7

Comparison between crystal growing and powder sintering processes

| Process | Material | Dimensions | Time | Cost | Process difficulty |
|---|---|---|---|---|---|
| Crystal growing | $MgF_2$ | Monocrystal 10-20 cm (maximum diameter) | Half a year or so | 5,000,000 yuan or so | Difficult |
| | $AlF_3$ | Monocrystal 10-20 cm (maximum diameter) | Half a year or so | 5,000,000 yuan or so | Difficult |

TABLE 7-continued

Comparison between crystal growing and powder sintering processes

| Process | Material | Dimensions | Time | Cost | Process difficulty |
|---|---|---|---|---|---|
| | $CaF_2$ | Monocrystal 10-20 cm (maximum diameter) | Half a year or so | 5,000,000 yuan or so | Difficult |
| Spark plasma sintering | $MgF_2$ | According to actual dimensional requirement | 1 month or so | 500,000 yuan or so | Easy |
| | $AlF_3$ | According to actual dimensional requirement | 1 month or so | 500,000 yuan or so | Easy |
| | $CaF_2$ | According to actual dimensional requirement | 1 month or so | 500,000 yuan or so | Easy |
| Vacuum hot-press sintering | $MgF_2$ | According to actual dimensional requirement | 2 months or so | 1,000,000 yuan or so | Easy |
| | $AlF_3$ | According to actual dimensional requirement | 2 months or so | 1,000,000 yuan or so | Easy |
| | $CaF_2$ | According to actual dimensional requirement | 2 months or so | 1,000,000 yuan or so | Easy |
| Hot isostatic pressure sintering | $MgF_2$ | According to actual dimensional requirement | 2-2.5 months | 500,000 yuan or so | Easy |
| | $AlF_3$ | According to actual dimensional requirement | 2-2.5 months | 500,000 yuan or so | Easy |
| | $CaF_2$ | According to actual dimensional requirement | 2-2.5 months | 500,000 yuan or so | Easy |

Note:
Except the main materials of powder, the above table omits 0.1 to 5 percent of $^6$LiF powder which is added in each main material, and although the above table only lists the three moderator materials, i.e. $MgF_2$ + LiF, $AlF_3$ + LiF and $CaF_2$ + LiF, and adopts the parameters of the above processes for comparison, as known well by those skilled in the art, other moderator materials, such as $Al_2O_3$ + LiF, can also be easily compared.

Known from the above table, although the density of the moderator material prepared by adopting the crystal growing method can approximate theoretical density, for example, reaching 99.99 percent of theoretical density, as the size of a monocrystal is small, in order to achieve a target large-size moderator material, multiple monocrystals need to be put together, other steps, such as mirror polishing, may need to be carried out on the moderator material in the process as well, and as a result, not only is a great deal of time consumed, but also both the cost and the process difficulty are great.

The density of the moderator material prepared by adopting the powder sintering method can also reach 80 to 100 percent of theoretical density. As a preference, the density of the moderator material reaches 99.99 percent of theoretical density. While there is almost no difference between the theoretical density and the theoretical density of the moderator material obtained by the crystal growing method, it has remarkable advantages in terms of obtained dimensions, time, cost and process difficulty. The actual dimensions of a moderator material prepared by adopting spark plasma sintering can be obtained according to requirement, one method can customize a desirable mold, the other method adopts an ordinary mold, such as a mold which is 70 cm in diameter and 2 cm in thickness, and multiple pieces are then put together, and under the premise that both the cost and the process difficulty are about the same as that of vacuum hot-press sintering and hot isostatic pressure sintering, its production time is only about one month.

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

What is claimed is:

1. A beam shaping assembly for neutron capture therapy comprising:

a beam inlet;

a target, wherein the target has nuclear reaction with an incident proton beam from the beam inlet to produce neutrons, and wherein the neutrons form a neutron beam defining a main axis;

a moderator adjoining to the target, wherein the neutrons are moderated by the moderator to epithermal neutron energies, the material of the moderator is prepared by mixing a mixture containing one or more of $PbF_4$, $Al_2O_3$, $AlF_3$, $CaF_2$ and $MgF_2$ and a $^6$Li element-containing material accounting for 0.1 to 5% in percentage by weight of the mixture;

a reflector surrounding the moderator, wherein the reflector leads the neutrons deviated from the main axis back to enhance epithermal neutron beam intensity;

a radiation shield for shielding leaking neutrons and photons so as to reduce dose of the normal tissue not exposed to irradiation; and a beam outlet.

2. The beam shaping assembly for neutron capture therapy according to claim 1, wherein the $^6$Li element-containing material is $^6$LiF or $^6$Li$_2$CO$_3$.

3. The beam shaping assembly for neutron capture therapy according to claim 1, wherein the material of the moderator is prepared by mixing $MgF_2$ and a $^6$Li element-containing material accounting for 0.1 to 5% in percentage by weight of the $MgF_2$.

4. The beam shaping assembly for neutron capture therapy according to claim 1, wherein the incident proton beam is accelerated by means of an accelerator and generate nuclear reaction with the target made of a metal material to produce neutrons, wherein the target is received into the moderator, wherein a gap channel for enhancing epithermal neutron beam intensity is arranged between the moderator and the reflector.

5. The beam shaping assembly for neutron capture therapy according to claim 1, wherein the beam shaping assembly further comprises a thermal neutron absorber for absorbing thermal neutrons so as to avoid overdosing in superficial normal tissue during therapy, the thermal neutron absorber is made of a material having a cross section for acting with thermal neutrons, and the reflector is made of a material having a high neutron reflection ability.

6. The beam shaping assembly for neutron capture therapy according to claim 5, wherein the reflector is made of at least one of Pb or Ni, the radiation shield comprises photon shield made of Pb and neutron shield made of PE, the thermal neutron absorber is made of $^6$Li, and wherein an air passage is arranged between the thermal neutron absorber and the beam outlet.

7. The beam shaping assembly for neutron capture therapy according to claim 1, wherein an outer surface of the moderator includes at least a tapered section.

8. The beam shaping assembly for neutron capture therapy according to claim 7, wherein an outer surface of the moderator includes a first tapered section and a second tapered section adjoining to the first tapered section, and a tapering direction of the first tapered section is opposite to a tapering direction of the second tapered section, and wherein the first tapered section includes a first side and a second side facing away from the beam outlet and is tapered gradually from the second side towards the first side, and the second tapered section includes a third side and a fourth side facing the beam outlet and is tapered gradually from the third side towards the fourth side, a distance from the target to the beam outlet is closer than a distance from the first side to the beam outlet.

9. The beam shaping assembly for neutron capture therapy according to claim 8, wherein the first side defines a first diameter perpendicularly to the main axis, the second side and the third side defines a second diameter perpendicularly to the main axis and the fourth side defines a third diameter perpendicularly to the main axis, the first diameter is 1 cm to 20 cm in length, the second diameter is 30 cm to 100 cm in length, the third diameter is 1 cm to 50 cm in length, and wherein multiple sintered blocks are connected to form the moderator and a density of the moderator is 80 to 100 percent of theoretical density.

10. A beam shaping assembly for neutron capture therapy comprising a moderator for neutrons, wherein the neutrons are moderated by the moderator to epithermal neutron energies, the material of the moderator is prepared by mixing a mixture containing one or more of PbF$_4$, Al$_2$O$_3$, AlF$_3$, CaF$_2$ and MgF$_2$ and a $^6$Li element-containing material accounting for 0.1 to 5% in percentage by weight of the mixture.

11. The beam shaping assembly for neutron capture therapy according to claim 10, wherein the $^6$Li element-containing material is $^6$LiF or $^6$Li$_2$CO$_3$.

12. The beam shaping assembly for neutron capture therapy according to claim 11, wherein the material of the moderator is prepared by mixing MgF$_2$ and $^6$LiF accounting for 0.1 to 5% in percentage by weight of the MgF$_2$.

13. The beam shaping assembly for neutron capture therapy according to claim 10, wherein the moderator is powder sintered block from powders or powder compacts.

14. The beam shaping assembly for neutron capture therapy according to claim 10, wherein an outer surface of the moderator includes a first tapered section and a second tapered section adjoining to the first tapered section, and a tapering direction of the first tapered section is opposite to a tapering direction of the second tapered section, and wherein the first tapered section includes a first side and a second side facing away from the beam outlet and is tapered gradually from the second side towards the first side, and the second tapered section includes a third side and a fourth side facing the beam outlet and is tapered gradually from the third side towards the fourth side.

15. The beam shaping assembly for neutron capture therapy according to claim 14, wherein the first side defines a first diameter perpendicularly to the main axis, the second side and the third side defines a second diameter perpendicularly to the main axis and the fourth side defines a third diameter perpendicularly to the main axis, the first diameter is 1 cm to 20 cm in length, the second diameter is 30 cm to 100 cm in length, the third diameter is 1 cm to 50 cm in length, and wherein multiple sintered blocks are connected to form the moderator and a density of the moderator is 80 to 100 percent of theoretical density.

16. The beam shaping assembly for neutron capture therapy according to claim 10, wherein an outer surface of the moderator includes a cylindrical section and a tapered section adjoining to the cylindrical section.

17. A beam shaping assembly for neutron capture therapy comprising a neutron moderating material, wherein the neutron moderating material is prepared by mixing a mixture containing one or more of PbF$_4$, Al$_2$O$_3$, AlF$_3$, CaF$_2$ and MgF$_2$ and a $^6$Li element-containing material accounting for 0.1 to 5% in percentage by weight of the mixture.

18. The beam shaping assembly for neutron capture therapy according to claim 17, wherein the $^6$Li element-containing material is $^6$LiF or $^6$Li$_2$CO$_3$.

19. The beam shaping assembly for neutron capture therapy according to claim 18, wherein the neutron moderating material is prepared by mixing MgF$_2$ and $^6$LiF accounting for 0.1 to 5% in percentage by weight of the MgF$_2$.

20. The beam shaping assembly for neutron capture therapy according to claim 17, wherein the neutron moderating material is powder sintered block from powders or powder compacts.

* * * * *